United States Patent [19]

Griffith et al.

[11] 3,937,831
[45] Feb. 10, 1976

[54] CHLOROMETHYL NITROPYRIDINES AS ANTIMICROBIALS

[75] Inventors: Jeffrey D. Griffith, Lafayette; Helen K. Tobol, Concord, both of Calif.

[73] Assignee: The Dow Chemical Company, Midland, Mich.

[22] Filed: Nov. 7, 1974

[21] Appl. No.: 521,615

Related U.S. Application Data

[63] Continuation-in-part of Ser. No. 386,653, Aug. 8, 1973, abandoned.

[52] U.S. Cl. ............... 424/263; 44/63; 106/15 R; 162/161; 252/106; 252/107; 260/45.8 N
[51] Int. Cl.$^2$ ............................................. A01N 9/22
[58] Field of Search ........................ 424/263; 71/94

[56] References Cited
UNITED STATES PATENTS
3,699,108   10/1972   Domenico ...................... 424/263

OTHER PUBLICATIONS
Hurst, J., J. Chem. Soc. (C), (1968), pp. 1487–1490.

Primary Examiner—V. D. Turner
Attorney, Agent, or Firm—S. Preston Jones

[57] ABSTRACT

Chloromethyl nitropyridine compounds which correspond to one of the formulae

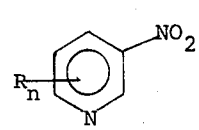 or 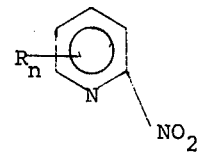

wherein R represents dichloromethyl, trichloromethyl and *n* represents an integer of 1 or 2, with the proviso that when *n* is 2, the R groups are not ortho to each other, and compositions containing said compounds are employed as broad spectrum antimicrobials for the control of both fungal and bacterial organisms.

10 Claims, No Drawings

CHLOROMETHYL NITROPYRIDINES AS ANTIMICROBIALS

CROSS REFERENCE TO RELATED APPLICATION

This application is a continuation-in-part of application Ser. No. 386,653, filed Aug. 8, 1973, now abandoned.

PRIOR ART

Various nitropyridines are known in the prior art, and such known compounds include various amino substituted nitro(trifluoromethyl)pyridines taught in U.S. Pat. Nos. 3,132,019; 3,495,969 and 3,634,439; various substituted nitropyridines taught in U.S. Pat. Nos. 3,574,841; 3,252,858; 3,547,935; 3,629,472 and 3,630,714; various halo nitro(trifluoromethyl)pyridines taught as bactericides and fungicides in U.S. Pat. No. 3,699,108, other compounds known in the prior art include mono- and dibromomethyl-nitropyridine taught in Hurst, et al., J. Chem. Soc. (C) 1968, pages 1487–1490.

SUMMARY OF THE INVENTION

The present invention is directed to the use of chloromethyl nitropyridines and compositions containing said compounds as broad spectrum antimicrobials. The chloromethyl nitropyridines employed are those corresponding to one of the formulae

In these and succeeding formulae, R represents dichloromethyl or trichloromethyl and $n$ represents an integer of 1 or 2, with the proviso that when $n$ is 2, the R groups are not ortho to each other.

The chloromethyl nitropyridines employed in the present invention are crystalline solids or oils which are not soluble in water and are soluble in many common organic solvents.

Representative compounds employed in the present invention include 3-(Dichloromethyl)-2-nitropyridine;
4-(Dichloromethyl)-2-nitropyridine;
5-(Dichloromethyl)-2-nitropyridine;
6-(Dichloromethyl)-2-nitropyridine;
3-(Trichloromethyl)-2-nitropyridine;
4-(Trichloromethyl)-2-nitropyridine;
5-(Trichloromethyl)-2-nitropyridine;
6-(Trichloromethyl)-2-nitropyridine;
2-(Dichloromethyl)-3-nitropyridine;
4-(Dichloromethyl)-3-nitropyridine;
5-(Dichloromethyl)-3-nitropyridine;
6-(Dichloromethyl)-3-nitropyridine;
3,5-Bis(dichloromethyl)-2-nitropyridine;
3,6-Bis(dichloromethyl)-2-nitropyridine;
4,6-Bis(dichloromethyl)-2-nitropyridine;
2,4-Bis(dichloromethyl)-3-nitropyridine;
2,5-Bis(dichloromethyl)-3-nitropyridine;
2,6-Bis(dichloromethyl)-3-nitropyridine;
4,6-Bis(dichloromethyl)-3-nitropyridine;
3-(Dichloromethyl)-5-(trichloromethyl)-2-nitropyridine;
3-(Dichloromethyl)-6-(trichloromethyl)-2-nitropyridine;
4-(Dichloromethyl)-6-(trichloromethyl)-2-nitropyridine;
3-(Trichloromethyl)-5-(dichloromethyl)-2-nitropyridine;
3-(Trichloromethyl)-6-(dichloromethyl)-2-nitropyridine;
4-(Trichloromethyl)-6-(dichloromethyl)-2-nitropyridine;
2-(Dichloromethyl)-4-(trichloromethyl)-3-nitropyridine;
2-(Dichloromethyl)-5-(trichloromethyl)-3-nitropyridine;
2-(Dichloromethyl)-6-(trichloromethyl)-3-nitropyridine;
4-(Dichloromethyl)-6-(trichloromethyl)-3-nitropyridine;
2-(Trichloromethyl)-4-(dichloromethyl)-3-nitropyridine;
2-(Trichloromethyl)-5-(dichloromethyl)-3-nitropyridine;
2-(Trichloromethyl)-6-(dichloromethyl)-3-nitropyridine;
4-(Trichloromethyl)-6-(dichloromethyl)-3-nitropyridine;
3,5-Bis(trichloromethyl)-2-nitropyridine;
3,6-Bis(trichloromethyl)-2-nitropyridine;
4,6-Bis(trichloromethyl)-2-nitropyridine;
2,4-Bis(trichloromethyl)-3-nitropyridine;
2,5-Bis(trichloromethyl)-3-nitropyridine;
2,6-Bis(trichloromethyl)-3-nitropyridine; and
4,6-Bis(trichloromethyl)-3-nitropyridine.

The chloromethyl nitropyridine compounds have been found to be of high toxicity to many bacterial or fungal organisms such as, for example, *Staphylococcus aureus, Escherichia coli, Candida albicans, Trichophyton mentagrophytes, Bacillus subtilis, Aspergillus terreus, Aerobacter aerogenes, Candida pelliculosa, Pullularia pullulans, Salmonella typhosa, Mycobacterium phlei, Pseudomonas aeroginosa, Pseudomonas sp.* Strain 10, *Rhizopus nigricans, Ceratocystis ips, Cephaloascus fragans, Trichoderm sp.* and *Rhizoctonia solani*. The compounds are of low toxicity to terrestrial plants and may be applied to many plants and their habitats in bactericidal and fungicidal amounts to obtain excellent controls of the microbial organisms which attack the seeds, roots or above-ground portions of terrestrial plants. Such practice protects the terrestrial plants and seeds and improves crop yield and the emergence and growth of seedlings. In further operations, it has been found that the compounds may be included in adhesives, cooling waters, inks, plasticizers, latices, resinous polymeric materials, fuels, greases, soaps, detergents, shampoos, cutting oils and oil or latex paints to prevent mold and mildew and the degradation of such products resulting from microbial attack. By resinous polymeric materials is meant natural and synthetic resinous polymers and plastic compositions or films derived therefrom. Also, the compounds advantageously may be distributed in natural and synthetic fabrics, and paper or other cellulosic products, or may be employed in the impregnation of wood, lumber, wallboard, and plaster to protect such products from the attack of the bacterial organisms of rot, mold, mildew and decay.

The dichloromethyl and trichloromethyl containing nitropyridine compounds of the present invention can be prepared by the liquid phase chlorination of an appropriate nitropicoline or nitrolutidine at atmospheric or superatmospheric pressures. In carrying out the preparation employing ordinary liquid phase chlorination techniques, an appropriate nitropicoline or nitrolutidine is contacted with gaseous chlorine in the presence of an inert solvent, such as, for example, carbon tetrachloride, chloroform, perchloroethylene or other non-reactive chlorination solvents conventionally employed for liquid phase chlorination reactions. The reaction is carried out at atmospheric pressure and at temperatures of from about 20°C. to about 120°C. and usually in the presence of actinic radiation.

In following the progress of the reaction, vapor phase chromatography is usually employed to determine the degree of completion. Upon completion of the reaction, usually in about 4 to about 8 hours, the product is recovered from the reaction mixture by conventional techniques of crystallization and evaporation of the solvent under reduced pressure.

In carrying out the process employing presure chlorination techniques, a mixture of an appropriate nitropicoline or nitrolutidine, an inert solvent, such as one of those set forth above, and a catalytic amount of a catalyst such as sulfuryl chloride are charged to a pressure reaction vessel and the temperature of the mixture is brought up to about 50°C. to about 120°C. Gaseous chlorine is charged to the vessel in an amount sufficient to provide a chlorine pressure of between about 250 to about 300 psig (pounds per square inch gauge). After a suitable reaction period (from about 4 to about 48 hours), the reaction vessel is vented and the product recovered from the reaction mixture by evaporation of the solvent therefrom under reduced pressure.

The products of the above preparation techniques can be purified if desired by conventional techniques of solvent washing and/or recrystallization from solvents such as hexane, chloroform, methylene chloride, pentane or mixtures thereof.

In the protection and preservation of inks, adhesives, soaps, detergents, greases, fuels, cutting oils, texiles, fabrics, latices, resinous plasticizers, polymeric materials and paper, good results are obtained when the compounds are incorporated in such products in the amount of from about 0.0001 to about 50 percent by weight.

In the protection of seeds, good results are obtained when the seeds are treated with the compounds at a dosage of about 2 to about 8 ounces per 100 pounds of seed. In addition to the direct treatment of seeds for their protection, the compounds are adapted to be readily and conveniently distributed in soil for the rapid control of soil-borne fungi.

The distribution of at least a minimum effective dosage of the chloromethyl nitro pyridine compounds in soil is essential for the practice of the present invention. In determining an effective dosage of the active compounds, at least a fungicidal amount of the desired toxicant should be employed. In general, good control of the fungal organisms is obtained when the compounds are distributed in the soil in the amount of from about 1.5 to 50 parts or more by weight per million parts by weight of soil. However, the effective amount of the compound to be employed will vary according to the compound being employed and according to the quantity of soil treated.

In field applications, the compounds may be distributed in the soil by broadcast methods wherein the entire field is treated, or in row applications wherein the row area to be planted is treated. In broadcast methods, the compounds can be distributed at a dosage of 2.5 to 500 pounds per acre. Such dosages are employed through a cross-section of the soil as to provide for the presence therein of an effective concentration of the treating agent. In other applications, the compounds can be distributed in the rows where the crop is to be planted. In such row treatment the compounds can be employed at a rate of from about 1 to about 5 pounds per acre. In field application any of the conventional methods such as drenching, drilling, row placement, etc. may be used to distribute the chemical in the soil at a dosage of 2.5 to 500 lb. per acre for the surface area of the soil actually treated to produce effective control of soil fungi. This does not, however, limit the application methods to those conventionally practiced.

The quantity of treating compositions to be applied to the soil may vary considerably provided that the required dosage of active ingredient is applied to facilitate the penetration and distribution of said ingredient in growth media. The required amount of the active ingredient in the soil conveniently may be supplied per acre treated in from 1 quart to 20 gallons or more of the liquid carrier, dispersed in 6 or more acre inches of irrigation water, or in from 50 to 2,000 pounds of inert solid carrier. A quantity of chemical is applied to produce a beneficial concentration in the quantity of soil treated.

In the preservation of wood, wallboard and plaster excellent results are obtained when the compounds are incorporated by conventional treatment of these products in the amount of from about 0.05 to about 3 pounds or more per cubic foot (0.0016 g./cc.) of wood, wallboard or plaster product. In the treatment of fruit, good results are obtained with liquid washes containing from about 1 to about 100 parts per million by weight of compound.

In the preservation and protection of oil and latex paints and primers against destruction caused by the growth of bacteria, the compounds are preferably employed at concentrations of from about 0.01 to about 3 percent by weight.

The method of the present invention can be carried out employing unmodified compounds or by employment of liquid or dust compositions containing the toxicants. In such usage, the compounds are modified with one or a plurality of chemically inert additaments or adjuvants including water, organic solvents, petroleum oils, petroleum distillates, naphthas or other liquid carriers, polymeric thickening agents, urea, surface-active dispersing agents and finely divided inert solids. In compositions wherein the adjuvant or helper is a finely divided solid, a surface-active agent or the combination of a surface-active agent and a liquid diluent, the carrier cooperates with the active component so as to facilitate the invention and to obtain an improved result.

The exact concentration of the toxicants to be employed in the treating compositions is not critical and may vary considerably provided the required dosage of the effective agent is supplied. The concentration of toxicant in liquid compositions generally is from 0.0001 to 50 percent by weight. Concentrations up to 95 percent by weight are oftentimes conveniently employed. In dusts, the concentrations of the toxicant can be from about 0.1 to 95 percent by weight. In compositions to be employed as concentrates, the toxicants can be present in a concentration of from 5 to 98 percent by weight.

In further embodiments, the compounds as employed in accordance with the present invention, or compositions containing the same, can be advantageously employed in the present invention in combination with one ore more pesticidal or preservative compounds to obtain products of enhanced properties. In such embodiments, such pesiticidal or preservative compounds are employed either as a supplemental toxicant, an additament or as an adjuvant. Representative pesticidal or preservative compounds include substituted phenols, cresols, substituted cresols and their heavy metal salts, bisphenols and thiobisphenols; halogenated salicylanilides, organosulfur compounds, carbamate compounds, quaternary ammonium compounds, organometallic compounds, inorganic salts and miscellaneous other compounds such as phenol; cresol; trichlorophenols; tetrachlorophenols; pentachlorophenol; p-chloro-m-cresol; di- and tribrominated salicylanilides; 2,2'-methylene-bis(3,4,6-trichlorophenol); 2,2'-thiobis(4,6-dichlorophenol); 1-(3-chloroallyl)-3,5,7-triaza-1-azoniaadamantane chloride; halo(alkylsulfonyl)pyridines; halo(alkylsulfinyl)pyridines; 2,4',5-tribromosalicylanilide; 2-chloro-4-cyclohexylphenol; 2-chloro-4-cyclopentylphenol; 2,2'-bis(3,4,6-trichlorophenyl)methane; 2,2'-bis(5-chloro-2-hydroxyphenyl)methane; halogenated trifluoromethyl salicylanilide; zinc dimethyldithiocarbamate; 2-mercaptobenzothiazole; 3,5-dimethyltetrahydro-1,3,5-2H-thiadiazine-2-thione; 2,3-dinitro-1,4-dithiaanthraquinone; dodecyl pyridinium chloride; alkyl dimethyl benzyl ammonium chloride; dialkyl dimethyl ammonium chloride; phenylmercuric acetate; phenyl mercuric oleate; phenyl mercuric propionate; chloromethyoxy acetoxy mercuripropane; bis-tributyl tin oxide; bis-tripropyl tin oxide; copper pentachlorophenate; copper 8-hydroxyquinolate; mercuric chloride; boric acid; sodium borate; ethylmercuric chloride; 9-undecylenic acid; or 10,10'-oxybisphenoxarsine and 1,4-bromobisacetobutene.

DESCRIPTION OF SOME PREFERRED EMBODIMENTS

The following examples illustrate the present invention and the manner by which it can be practiced, but, as such, should not be construed as limitations upon the overall scope of the same.

EXAMPLE I

Various chloromethyl nitropyridine concentrates were prepared by admixing a predetermined amount of each of the compounds with a predetermined amount of isopropanol. These concentrates were thereafter dispersed in varying amounts of warm melted nutrient agar to prepare culture media containing one of said pyridine compounds in amounts of 1, 10, 100 and 500 parts per million parts of the ultimate dispersion (PPM). The melted agar dispersion was poured into petri dishes and allowed to solidify. The solidified surface in each dish was inoculated with a 24-hour broth culture of one of the organisms *Staphylococcus aureus, Escherichia coli, Candida albicans, Trichophyton mentagrophytes, Bacillus subtilis, Aspergillus terreus, Aerobacter aerogenes, Candida pelliculosa, Pullularia pullulans, Salmonella typhosa, Mycobacterium phlei, Pseudomonas aeruginosa, Pseudomonas sp* Strain 10, *Rhizopus nigricans, Ceratocystis ips, Cephaloascus fragans* and *Trichoderm sp*. In a check operation, petri dishes containing toxicant free nutrient agar are each inoculated in the same manner with the above named organisms. The dishes were thereafter incubated for 5 days after which they were observed to determine the minimum concentration of each compound tested to give 100 percent kill and control of the growth of the test organisms in the nutrient agar. At the time of these observations, the check dishes are found to support a heavy growth of the above named organisms. The results of these observations are set forth below in Table I.

TABLE I

| Compound Employed | Minimum Concentration of Test Compound in PPM Necessary to Give 100 Percent Control of the Organisms | | | | | | | | | | | | | | | |
|---|---|---|---|---|---|---|---|---|---|---|---|---|---|---|---|
| | Sa | Ca | Ec | Pa | Ps | St | Mp | Bs | Cp | Aa | Pp | Cf | Ci | Ts | At | Rn |
| 2-(Dichloromethyl)-6-(trichloromethyl)-3-nitropyridine | 1 | 10 | 100 | 500 | 500 | 100 | 1 | 1 | 10 | 100 | 10 | 10 | 10 | 100 | 10 | 10 |
| 5-(Dichloromethyl)-2-nitropyridine | 10 | 10 | 10 | 100 | 100 | 10 | 10 | 1 | 10 | 10 | 10 | 10 | 10 | 10 | 1 | 10 |
| 6-(Trichloromethyl)-3-nitropyridine | 10 | 1 | 100 | 100 | 100 | 10 | 10 | 1 | 10 | 10 | 100 | 10 | 1 | 10 | 10 | 10 |
| 6-(Dichloromethyl)-2-nitropyridine | 100 | 100 | 500 | — | — | 500 | 100 | 10 | 100 | 500 | 100 | 100 | 100 | 100 | 10 | 100 |

Sa = Staphylococcus aureus
Ca = Candida albicans
Ec = Escherichia coli
Pa = Pseudomonas aeruginosa
Ps = pseudomonas Sp. strain 10
St = Salmonella typhosa
Mp = Mycobacterium phlei
Bs = Bacillus subtilis
Cp = Candida pelliculosa
Aa = Aerobacter aerogenes
Pp = Pullularia pullulans
Cf = Cephaloascus fragans
Ci = Ceratocystis ips
Ts = Trichoderm Sp
At = Aspergillus terreus
Rn = Rhizopus nigricans
— = not tested

EXAMPLE II

An acetone solution of one of 6-(trichloromethyl)-3-nitropyridine, 5-(dichloromethyl)2-nitropyridine or 6-(trichloromethyl)-2-(dichloromethyl)-3-nitropyridine was employed for the treatment of sandy loam soil infested with a natural soil fungi population including *Rhizoctonia solani*. In such operation samples of the fungus-infested soil were placed in sealable containers and various acetone solutions of the toxicant were added to each sample in a concentration appropriate to provide the total soil sample in the container with an amount of one of 0.4, 1.5, 6 and 25 parts by weight of toxicant per million parts by weight of soil (PPM). At the same time, checks were prepared by treating containers of the same infested soil with an amount of acetone equal to that employed in the corresponding test containers. The soil samples were sealed and rolled to distribute the toxicant uniformly throughout the sample. After an incubation period of 3 days at 25°C. aliquot amounts of each soil sample were taken and diluted in sterile water blanks. Two drops of each of the resulting soil-water suspensions were placed in a petri dish to which 10 milliliters of rose bengal agar were added. The poured plates were incubated for 6 days at 25°C., following which they were examined and a count made of the total fungal colony population on each. The extent to which each toxicant effected control as compared with the checks, is shown in the following table:

TABLE II

| Toxicant Employed | Percent Control of Total Soil Fungi at Indicated Toxicant Concentration in PPM | | | |
|---|---|---|---|---|
| | .4 | 1.5 | 6 | 25 |
| 6-(trichloromethyl)-3-nitropyridine | 63 | 99 | 100 | 100 |
| 5-(dichloromethyl)-2-nitropyridine | 0 | 65 | 85 | 99 |
| 6-(trichloromethyl)-2-(dichloromethyl)-3-nitropyridine | 0 | 34 | 100 | 99 |
| Control | 0 | 0 | 0 | 0 |

EXAMPLE III

In this operation, containers containing *Rhizoctonia solani* infected, sandy loan soil samples were treated with an acetone solution of 6-(trichloromethyl)-3-nitropyridine by drenching onto the soil sample, a water diluted aliquot of the above toxicant in an amount sufficient to give soil sample containing 6, 25 and 100 parts by weight of the toxicant per million parts by weight of soil (PPM). In control operations, controls were prepared by treating containers of the same infected soil with an amount of acetone equal to the amount employed in the corresponding test containers. The containers were immediately sealed and incubated for 6 days at 25°C. The containers were thereafter unsealed and aerated. Five cotton seeds were planted on the top of the soil in each container and a sand cap added. The soil was moistened and placed in a room maintained at 25°C, under conditions of high humidity. At the end of 14 days, the containers were examined to determine the pre-emergent control of *Rhizoctonia solani* and at the end of 19 days, the resulting seedlings were evaluated to determine post-emergent control of the above organism, the activity of the test compound being determined by comparison with the control containers. The results of these determinations are set forth below in Table III.

TABLE III

| Compound Employed | Dosage of Active Compound in PPM in Soil | Control of Rhizoctonia solani | |
|---|---|---|---|
| | | Pre-Emergent | Post-Emergent |
| 6-(trichloromethyl)-3-nitropyridine | 100 | 100 | 100 |
| | 25 | 60 | 50 |
| | 6 | 60 | 20 |
| Acetone Control | — | 0 | 0 |

What is claimed is:

1. A method for killing microbes selected from the group consisting of bacteria and fungi which comprises contacting said microbes with an antimicrobial amount of a chloromethyl nitropyridine compound corresponding to one of the formulae

wherein R represents dichloromethyl or trichloromethyl and *n* represents an integer of 1 or 2, with the proviso that when *n* is 2, the R groups are not ortho to each other.

2. The method of claim 1 wherein the halomethyl nitropyridine is 6-(trichloromethyl)-2-(dichloromethyl)-3-nitropyridine.

3. The method of claim 1 wherein the halomethyl nitropyridine is 5-(dichloromethyl)-2-nitropyridine.

4. The method of claim 1 wherein the halomethyl nitropyridine is 6-(trichloromethyl)-3-nitropyridine.

5. The method of claim 1 wherein the halomethyl nitropyridine is 6-(dichloromethyl)-2-nitropyridine.

6. A method for killing soil fungi which comprises treating soil with a fungicidal amount of a chloromethyl nitropyridine compound corresponding to one of the formulae

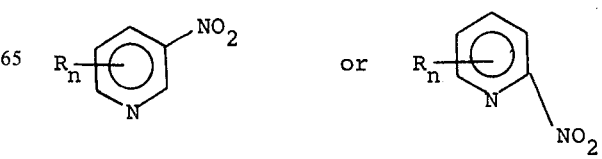

wherein R represents dichloromethyl or trichloromethyl and *n* represents an integer of 1 or 2, with the proviso that when *n* is 2, the R groups are not ortho to each other.

7. The method of claim 6 wherein the halomethyl nitropyridine is 6-(trichloromethyl)-2-(dichloromethyl)-3-nitropyridine.

8. The method of claim 6 wherein the halomethyl nitropyridine is 5-(dichloromethyl)-2-nitropyridine.

9. The method of claim 6 wherein the halomethyl nitropyridine is 6-(trichloromethyl)-3-nitropyridine.

10. The method of claim 6 wherein the halomethyl nitropyridine is 6-(dichloromethyl)-2-nitropyridine.

* * * * *